(12) United States Patent
Lawson et al.

(10) Patent No.: US 12,403,299 B2
(45) Date of Patent: *Sep. 2, 2025

(54) APPARATUSES, SYSTEMS, AND METHODS FOR THE TREATMENT OF DAMAGED TISSUE

(71) Applicant: Adlore, Inc., Kalamazoo, MI (US)

(72) Inventors: Daryl Lawson, Kalamazoo, MI (US); Christopher Brian Arena, Blacksburg, VA (US); Tim A. Fischell, Kalamazoo, MI (US)

(73) Assignee: Adlore, Inc., Kalamazoo, MI (US)

( * ) Notice: Subject to any disclaimer, the term of this patent is extended or adjusted under 35 U.S.C. 154(b) by 538 days.

This patent is subject to a terminal disclaimer.

(21) Appl. No.: 17/741,717

(22) Filed: May 11, 2022

(65) Prior Publication Data

US 2022/0265996 A1 Aug. 25, 2022

Related U.S. Application Data

(63) Continuation-in-part of application No. 17/324,705, filed on May 19, 2021, now Pat. No. 12,011,584, and
(Continued)

(51) Int. Cl.
*A61N 1/04* (2006.01)
*A61N 1/28* (2006.01)
*A61N 1/372* (2006.01)

(52) U.S. Cl.
CPC .......... *A61N 1/0484* (2013.01); *A61N 1/0468* (2013.01); *A61N 1/28* (2013.01); *A61N 1/37282* (2013.01)

(58) Field of Classification Search
CPC ...... A61N 1/0484; A61N 1/0468; A61N 1/28; A61N 1/37282; A61N 1/326;
(Continued)

(56) References Cited

U.S. PATENT DOCUMENTS 5,974,342 A 10/1999 Petrofsky
6,094,599 A 7/2000 Bingham et al.
(Continued)

FOREIGN PATENT DOCUMENTS

WO 2007088348 A2 8/2007
WO WO-2017190049 A1 * 11/2017 ............. A43B 17/00

OTHER PUBLICATIONS

International Search Report for PCT/US2019/16596 dated Apr. 30, 2019; 2 pages.
(Continued)

*Primary Examiner* — Ankit D Tejani
*Assistant Examiner* — Joshua Brendon Solomon
(74) *Attorney, Agent, or Firm* — Gardner, Linn, Burkhart & Ondersma LLP

(57) ABSTRACT

A therapeutic apparatus for treating damaged tissue on a limb or body of a subject includes a wearable adapted to cover and be secured to the limb or body of a subject over damaged tissue. The wearable being configured to reduce pressure on the damaged tissue and adapted to deliver one or more treatments selected from the group consisting of heat, oxygen, electrical current, and light to the damaged tissue.

24 Claims, 9 Drawing Sheets

Related U.S. Application Data a continuation of application No. 17/004,243, filed on Aug. 27, 2020, now Pat. No. 11,338,128, said application No. 17/324,705 is a continuation of application No. 16/267,635, filed on Feb. 5, 2019, now Pat. No. 1,101,910.

(60) Provisional application No. 62/893,025, filed on Aug. 28, 2019, provisional application No. 62/627,028, filed on Feb. 6, 2018.

(58) Field of Classification Search
CPC ...... A61F 2007/0042; A61F 2007/0043; A61F 2007/0045; A61F 2007/0071; A61F 2007/0249; A61F 7/007; A61F 7/02
See application file for complete search history.

(56) References Cited

U.S. PATENT DOCUMENTS

| | | | |
|---|---|---|---|
| 7,144,390 B1 | 12/2006 | Hannigan et al. | |
| 7,483,738 B2 | 1/2009 | Tamarkin et al. | |
| 7,540,848 B2 | 6/2009 | Hannigan et al. | |
| 7,689,285 B2 | 3/2010 | Garabet | |
| 8,372,022 B2 | 2/2013 | Hannigan et al. | |
| 8,388,562 B2 | 3/2013 | Baker et al. | |
| 8,827,941 B2 | 9/2014 | Davis et al. | |
| 8,840,573 B2 | 9/2014 | Neustaedter et al. | |
| 8,882,687 B2 | 11/2014 | Hannigan et al. | |
| 9,333,282 B2 | 5/2016 | Van der Hulst | |
| 9,526,816 B2 | 12/2016 | Toth | |
| D787,077 S | 5/2017 | Lindsay | |
| 9,642,414 B2 | 5/2017 | Lindsay et al. | |
| 9,724,243 B2 | 8/2017 | Hannigan et al. | |
| 10,058,478 B2 | 8/2018 | Schnetz et al. | |
| 10,130,805 B2 | 11/2018 | Schonenberger et al. | |
| 10,166,387 B2 | 1/2019 | Bergelin et al. | |
| 10,206,604 B2 | 2/2019 | Bergelin et al. | |
| 10,207,031 B2 | 2/2019 | Toth | |
| 11,338,128 B2 * | 5/2022 | Lawson | A61N 5/0625 |
| 2002/0026226 A1 | 2/2002 | Ein | |
| 2004/0173220 A1 * | 9/2004 | Harry | A43B 7/00 128/892 |
| 2004/0254624 A1 | 12/2004 | Johnson | |
| 2005/0015124 A1 | 1/2005 | Irwin | |
| 2007/0016271 A1 | 1/2007 | Hammond | |
| 2007/0179585 A1 * | 8/2007 | Chandler | A61N 1/326 623/1.1 |
| 2007/0264354 A1 | 11/2007 | Herman | |
| 2007/0282400 A1 | 12/2007 | Gorham | |
| 2008/0027509 A1 | 1/2008 | Andino et al. | |
| 2009/0240216 A1 | 9/2009 | Hannigan et al. | |
| 2010/0210983 A1 | 8/2010 | Baker et al. | |
| 2010/0234837 A1 | 9/2010 | Alfano | |
| 2010/0268300 A1 | 10/2010 | Ramos Leal et al. | |
| 2010/0292746 A1 | 11/2010 | Gorham | |
| 2010/0318018 A1 | 12/2010 | Schonenberger et al. | |
| 2011/0125204 A1 | 5/2011 | Louise | |
| 2011/0213319 A1 | 9/2011 | Blott et al. | |
| 2011/0214315 A1 | 9/2011 | Mayer et al. | |
| 2012/0259266 A1 * | 10/2012 | Quisenberry | A61M 37/00 604/20 |
| 2012/0316480 A1 | 12/2012 | Nolan et al. | |
| 2013/0158634 A1 | 6/2013 | Ron Edoute et al. | |
| 2013/0274629 A1 | 10/2013 | Duesterhoft et al. | |
| 2013/0304007 A1 | 11/2013 | Toth | |
| 2013/0326912 A1 | 12/2013 | Lindsay et al. | |
| 2014/0052054 A1 | 2/2014 | Qunsenberry | |
| 2014/0206947 A1 | 7/2014 | Isserow et al. | |
| 2015/0075030 A1 | 3/2015 | Walborn et al. | |
| 2016/0015962 A1 | 1/2016 | Shokoueinejad Maragheh et al. | |
| 2016/0045735 A1 | 2/2016 | Chang et al. | |
| 2016/0058999 A1 | 3/2016 | Skiba | |
| 2016/0081580 A1 | 3/2016 | Bergelin et al. | |
| 2016/0143555 A1 | 5/2016 | Decre et al. | |
| 2016/0184575 A1 | 6/2016 | Schonenberger et al. | |
| 2016/0213521 A1 | 7/2016 | Bacon et al. | |
| 2016/0213552 A1 | 7/2016 | Lindsay | |
| 2017/0056233 A1 | 3/2017 | Kelly | |
| 2017/0128117 A1 | 5/2017 | Myers et al. | |
| 2017/0296805 A1 | 10/2017 | Mower | |
| 2018/0008000 A1 | 1/2018 | Chanda et al. | |
| 2019/0134396 A1 * | 5/2019 | Toth | A61N 1/0456 |
| 2019/0240475 A1 | 8/2019 | Lawson et al. | |
| 2019/0297992 A1 | 10/2019 | Raza et al. | |
| 2019/0388667 A1 | 12/2019 | Xu | |

OTHER PUBLICATIONS

Written Opinion of the International Searching Authority for PCT/US2019/16596 dated Apr. 30, 2019; 5 pages.
International Search Report for PCT/US2020/48087 dated Nov. 20, 2020; 2 pages.
Written Opinion of the International Searching Authority for PCT/US2020/48087 dated Nov. 20, 2020; 20 pages.
Supplemental European Search Report from corresponding European Application No. 20857765.0, completed Aug. 8, 2023.

* cited by examiner

APPARATUSES, SYSTEMS, AND METHODS FOR THE TREATMENT OF DAMAGED TISSUE

This application is a continuation of U.S. patent application Ser. No. 17/004,243, now U.S. Pat. No. 11,338,128, filed Aug. 27, 2020, by inventors Daryl Lawson et al. and entitled APPARATUSES, SYSTEMS, AND METHODS FOR THE TREATMENT OF DAMAGED TISSUE, which claims the benefit of U.S. Prov. Pat. App. Ser. No. 62/893,025, filed Aug. 28, 2019, by inventors Daryl Lawson et al. and entitled APPARATUSES, SYSTEMS, AND METHODS FOR THE TREATMENT OF DAMAGED TISSUE, which are all incorporated by reference in their entireties herein. This application is also a continuation-in-part of U.S. patent application Ser. No. 17/324,705, now U.S. Pat. No. 12,011,584, filed May 19, 2021, entitled DEVICES, METHODS, AND SYSTEMS FOR THE TREATMENT AND/OR MONITORING OF DAMAGED TISSUE, which is a continuation of U.S. patent application Ser. No. 16/267,635, filed Feb. 5, 2019, entitled DEVICES, METHODS, AND SYSTEMS FOR THE TREATMENT AND/OR MONITORING OF DAMAGED TISSUE, now U.S. Pat. No. 11,013,910, which claims the benefit of U.S. Provisional Application Ser. No. 62/627,028, filed on Feb. 6, 2018, entitled DEVICE, METHODS, AND SYSTEM FOR THE TREATMENT OF WOUNDS, which are all incorporated by reference in their entireties herein.

TECHNICAL FIELD AND BACKGROUND

This disclosure relates to apparatuses, systems, and methods for the treatment of damaged tissue.

Pressure ulcers, such diabetic foot ulcers (DFUs), are the cause of over 108,000 amputations each year in the United States. The number of people who lose a limb due to diabetes is expected to triple by the year 2050. Nationally, of the over $327 billion spent annually on managing diabetes, and $9.0 to $13.0 billion is linked to the treatment of DFUs.

Often, poor-healing, neuropathic wounds that occur on diabetic patients, especially on the lower extremities, will only worsen if left untreated, in part due to impairment of blood flow resulting in poor circulation and nerve damage. Patients who have diabetes experience nerve damage and reduced blood flow in the limbs, and ulcers often develop on the bottom of the foot.

Similarly, wounds resulting from surgery or an injury may also have trouble healing due to the age of a patient or condition of a patient, such as a diabetic patient.

There is, therefore, a need for treatment of damaged tissue, such as wounds or pressure sores or ulcers, especially DFUs, in a cost-effective manner that can prevent prolonged recovery, or in some cases amputation.

SUMMARY

Accordingly, apparatuses, methods, and systems are disclosed for treating damaged tissue, such as in a wound or ulcer.

In one embodiment, a therapeutic apparatus includes a wearable for a limb, such as a boot, or other body part, such as the sacrum region of the torso. The wearable is adapted to be secured to the limb or body of a subject and, further, is configured to reduce pressure on the damaged tissue. Further, the wearable is adapted to deliver one or more treatments of heat, electrical current, oxygen, and/or light, such as ultraviolet light (UV) light, to treat the damaged tissue.

In another embodiment, a therapeutic apparatus includes a wearable to be secured to a limb or other body part, such as the sacrum, and includes a pair of electrodes to apply electrical stimulation to the damaged tissue. The wearable is adapted to apply one or more treatments heat, oxygen, and/or light, such as UV light, to treat the damaged tissue.

In a third embodiment, a therapeutic apparatus for treating damaged tissue on a foot of a subject includes a wearable configured to cover at least the foot of the subject, with the wearable being configured to conform to the patient's foot and including a recess in the region of the damaged tissue to reduce pressure on the damaged tissue. The apparatus further includes a supply of one or more treatments of (1) electrical current to apply electrical stimulation to the damaged tissue, (2) heat to warm the foot at least locally at the damaged tissue, (3) oxygen to apply to the damaged tissue, and/or (4) light to apply a treatment to the damaged tissue.

For example, the recess may be formed by a through hole formed in the boot, such as in the sole of the boot when treating a wound in the bottom of the foot.

In any of the above, when electrical current is used, the electrical current may be supplied by at least two electrodes that are located so that they contact the skin of the patient when wearing the apparatus. The apparatus may have a voltage source that is in communication with the electrodes to supply current to the electrodes, which in turn then apply a current to the patients skin.

In any of the above, when heat is provided, the heat may be supplied by a heating component, which may dissipate heat throughout the wearable or be partially integrated into the apparatus.

For example, the heat component may be formed by conductive wiring that is integrated into the apparatus and further which is coupled to a voltage source.

In another example, the heating component may comprise one or more light sources, which are in communication with a voltage source to power the light source, which as noted generates heat to apply to the patients skin. Suitable light sources may be infrared lights, such as infrared LEDS.

In yet another example, the heating component may comprise a supply of fluid that is warmed and circulated though the apparatus. For example, the fluid may be warmed through a heating device external to the apparatus or a heating device at least partially integrate or mounted to the apparatus. The fluid may be liquid or a gas, such as air. Further, the fluid may be directed through channels formed in or tubing inserted into the apparatus.

In any of the above, the voltage source may be provided from an external source or by an on board voltage source, such as a capacitor or a battery, including a rechargeable battery, which may be integrated into the apparatus with an optional control module to control the voltage source (either at the voltage source or remotely) to supply voltage to the respective treatment component (s), and/or electrical leads with a plug configured to couple to a DC source, such as battery, or an AC source, such as a standard wall AC outlet.

In any of the above, when oxygen is provided, the oxygen may be supplied by tubing that is coupled to an oxygen gas source, such as a canister of oxygen, which may be mounted to or integrated into the wearable, or a liquid source of oxygen, such as supersaturated oxygenated saline, which may be supplied from a container, such as a bag, which again may be mounted to or integrated into the wearable. Alternately, the oxygen may be provided by a dressing saturated with liquid containing oxygen.

Regardless of the form, the oxygen is directed to or near the damaged tissue. When supplied as a liquid or gas, the oxygen may be directed to the damaged tissue at least initially by the tubing. For example, the tubing may be surfaced mounted or integrated into the apparatus. And when the apparatus has a recess located in the proximity of the damaged tissue, the tubing optionally directs the oxygen into the recess, which in addition to reducing pressure on the damaged tissue then forms a chamber over the damaged tissue between the patient's body and the apparatus (when the apparatus is secured to the patient over the damaged tissue).

In one embodiment, the oxygen may be delivered to the damaged tissue by a separate device and then the apparatus is placed over the separate device. For example, as noted above, the oxygen may be provided in the form of a dressing, which can either be mounted to the wearable or applied to the damaged tissue, which then enclosed by the wearable.

In any of the above, when UV light is applied, the UV light may be delivered by a UV light source, such as a UV LED. The lamp may be located in the apparatus so that it directly applies UV light to the damaged tissue or indirectly via a light pipe.

For example, the UV light may be formed from a plurality of UV LEDs, such as an array of UV LEDS, which are mounted about the damaged tissue, for example in or adjacent any recess that is provided or in the skin facing surface of the apparatus. Alternately, the LEDs may be mounted outside the apparatus, including being surface mounted, and optically coupled to a light pipe, such an optical fiber or fibers or a unitary plastic member, that directs light into and through the wearable and emits the UV light onto the damaged tissue.

For example, when the apparatus has a recess (e.g. as noted above to reduce pressure of the damage tissue), the light pipe may have a terminal light emitting end that extends to the perimeter of the recess so that it emits light into the chamber formed between the recess and the patient's skin.

In another embodiment, the terminal light emitting end may extend into the recess beyond the perimeter of the recess and direct the light onto the damaged tissue.

In another embodiment, the light source may provide dual functions—providing UV light and/or providing infrared light to warm the damaged tissue. These functions can occur at the same time or separately. For example, an array of LEDs may be provided with one set of LEDs providing UV light, and the other set of LEDs providing infrared light so that the LED source (array) is tunable between a UV light output and an infrared light output or output both.

In another embodiment, any of the apparatuses may further include one or more sensors. Optionally, at least one sensor is configured to measure at least one indicator of wound healing. Other sensors may be used to keep track of the use of the device and/or condition of the patient, e.g. heart rate, blood flow, respiration, temperature, activity, pH and/or when the patient is wearing the device (compliance).

The apparatus may also comprise at least one control unit to operate the various treatments described above.

In yet other aspects, any of the above apparatuses may include a transceiver for receiving control signals or sending information, such as data, about or relative to the apparatus, or to the patient, such as the state of the wound or the person, to a remote computer, such as a laptop computer, a hand held device, a nurse call station, or a server. For example, the information may include information about the use of the device or information about the damage tissue being treated or the patient being treated.

In another embodiment, a system for treating damaged tissue includes a therapeutic apparatus with a wearable of the types disclosed above, a control unit with a transmitter, and a remote control device in communication with the control unit. The control unit and/or the remote device are configured to control the various treatments described above.

For example, the remote control device may comprise a computer, such as a laptop computer, a handheld device, such as a smart device, including a smart phone, with an app configured to allow control over the therapeutic apparatus, with the control unit or the remote device being configured as the master control device, and the other as a slave control device.

For further details of the various embodiments of the apparatus, reference is made to the above.

In another aspect, a method of treating damaged tissue is disclosed. The method may comprise the steps of covering the damaged tissue with a wearable, configuring the wearable to reduce the stress on the damaged tissue, and applying one or more treatments of heat, electrical current, oxygen, and/or light, such as UV light, to treat the damaged tissue.

In one aspect, the method includes applying oxygen to the damaged tissue.

In a further aspect, the method includes further applying electrical simulation to the limb with the damaged tissue.

Optionally, the method may include generating electrical pulses and applying the electrical pulses to the limb to apply the electrical stimulation.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION

As will be more fully described below, disclosed herein are apparatuses, systems, and methods, for treating damaged tissue, including treating wounds, including ulcers, such as diabetic ulcers. The disclosed apparatuses, methods, and systems may reduce the risk of wound infection, treat infection, and/or promote healing of damaged tissue, such as wounds, via the joint application of reducing extrinsic pressure and one or more of electrical stimulation, oxygen, light, such as UV light, and/or heat. The apparatuses, methods, and systems may be embodied in a variety of ways. Further, although illustrated in reference to a human patient, it should be understood that the apparatuses, methods, and systems disclosed herein may also be used on animal patients.

Figure 1:
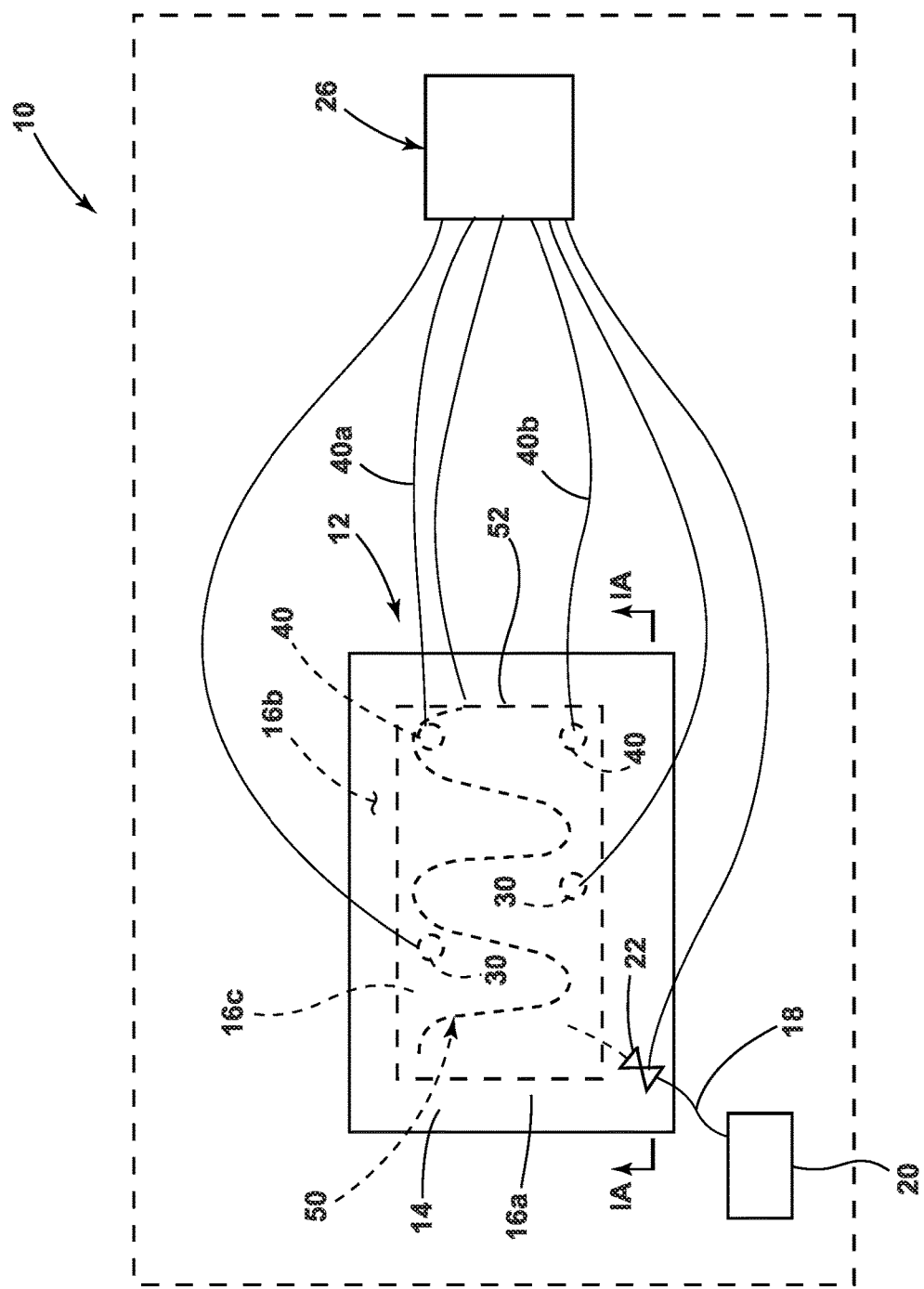
FIG. 1 is a schematic diagram illustrating one embodiment of an apparatus for treating damaged tissue.

Referring to FIG. 1, the numeral 10 generally designates a therapeutic apparatus for treating damaged tissue, such as a wound on a limb, including a foot, or body of a patient, such as the hips or tailbone. Apparatus 10 includes a wearable 12 adapted to cover and, optionally, be secured to the limb or body of the patient over the damaged tissue. The term "wearable" is used broadly herein and refers to something, like a patch or a cover or a pad, or the like, that can be worn by a patient with or without assistance from an adhesive or other mechanism to secure the wearable to the patient. In other words, it can be simply placed on the patient and, optionally, secured in place by the wearable itself (e.g. by an adhesive or sticky layer) or by other mechanisms.

In one embodiment, the wearable 12 is configured to reduce extrinsic pressure (for example, by eliminating added pressure on the wound or by redistributing pressure) on the damaged tissue to increase the blood flow to the damaged tissue, or conversely by removing pressure and hence removing possible constriction of the blood flow. In addition, wearable 12 is further configured to apply treatment the damage tissue to improve healing of the damaged tissue, for example, by stimulating more blood flow, increasing granulation, reducing hypoxia, and/or by increasing infection control. As will be more fully described below, the treatments may include applying electrical stimulation, applying oxygen, applying heat, and/or applying light, such as UV light, as well as medicaments, such as antimicrobial medicaments.

As noted above, in the illustrated embodiment, wearable 12 is configured to reduce extrinsic pressure on the damaged tissue—in other words not apply any additional outside (extrinsic) pressure above ambient pressure while still covering the damaged tissue. Referring again to FIG. 1, wearable 12 may be formed from a pad 14 of flexible material, such as a foam or rubber material, which forms an exterior surface 16a of wearable 12 on one side and a tissue facing surface 16b on its opposed side. Tissue facing surface 16b includes a region 16c that is adapted to reduce extrinsic pressure or not apply any extrinsic pressure to the wound. For example, region 16c may comprise a recess that sized to extend over and, optionally, extend beyond the perimeter of the damaged tissue (D, see FIG. 1A) to reach undamaged tissue surrounding the wound or wounds.

Where multiple areas of damaged tissue exist, then region 16c may optionally extend over an area that includes all, or most, of the damages tissue areas. Alternately, the tissue facing surface 16b may include multiple regions 16c that are adapted to reduce extrinsic pressure or not apply any extrinsic pressure. In some embodiments described below, the facing surface 16b may have a recess that is used as a chamber that can be at least periodically pressurized above ambient pressure for delivering treatment to the wound. When the recess is used as closed chamber (to apply a fluid), as more fully described below, layer 14a may comprise an impermeable flexible material, such as a closed cell foam or rubber, such as neoprene. When the recess not used as a closed chamber, layer 14a may comprise a liquid impermeable, but gas permeable material to allow the damaged tissue to breathe but to protect the damaged tissue from unintended liquid intrusion. For example, a suitable material may include a permeable foam, such as an open cell foam, including a reticulated foam. For example of other suitable materials reference is made to copending application, U.S. patent application Ser. No. 16/267,635, entitled DEVICES, METHODS, AND SYSTEMS FOR THE TREATMENT OF WOUNDS, filed Feb. 5, 2019, which is incorporated by reference it its entirety herein.

Alternately, or in addition, region 16c may be formed from or have an insert therein formed from a softer, more compressible material (for a given force) than the balance of the tissue facing side 16b. For example, the insert may be formed from a spongy material, such as a soft open cell foam. In this manner, when a patient's limb or body is resting on the wearable, the region 16c will not apply any extrinsic (additional) pressure (above ambient pressure) so that the pressure on the wound is just ambient pressure or greatly reduced (only slightly above ambient pressure). Instead, region 16c will compress and deflect sufficiently to redistribute all, if not most, of the extrinsic pressure to the surrounding healthy tissue.

In one embodiment, pad 14 may be formed from a 3D printing process based on a model of the body part being treated, with region 16c being removed from the 3D model using an editing tool. For example, the body part may be modeled using an imaging process, for example, using cameras, to create a 3D model of the body part and then the region corresponding to the wound may be selected and removed using the 3D printing editing tools so that when printed the recess in the pad is formed. Similarly, spaces or voids for holding the various treatment devices or conduits for delivering the treatments (s) may be removed during the editing processes. In addition, when an insert is desired in the recess, the insert can be modeled from the region that corresponds to the recess, e.g. edited region, so there is a precise fit between the insert and the recess in the pad. Optionally, the insert may be sized so that it is smaller than the recess to allow for expansion of the insert when the insert is filled with a fluid, more fully described below.

As noted above, the electrodes and/or associated circuitry and, in some cases, at least some of the sensors described below may be screen printed onto the wearable. Similarly, the circuitry for the sensors and other devices (e.g. heating component) may be screen printed so that the wearable is an integrated assembly. In one embodiment, when forming pad 14 from 3D printing, reliefs or recessed areas may be formed (e.g. using the editing tool) to accommodate the various surface mounted devices so that the device can be flush with the skin facing side of the pad, or in some cases recessed further so as not to make contact with the patient's skin.

Figure 1A:
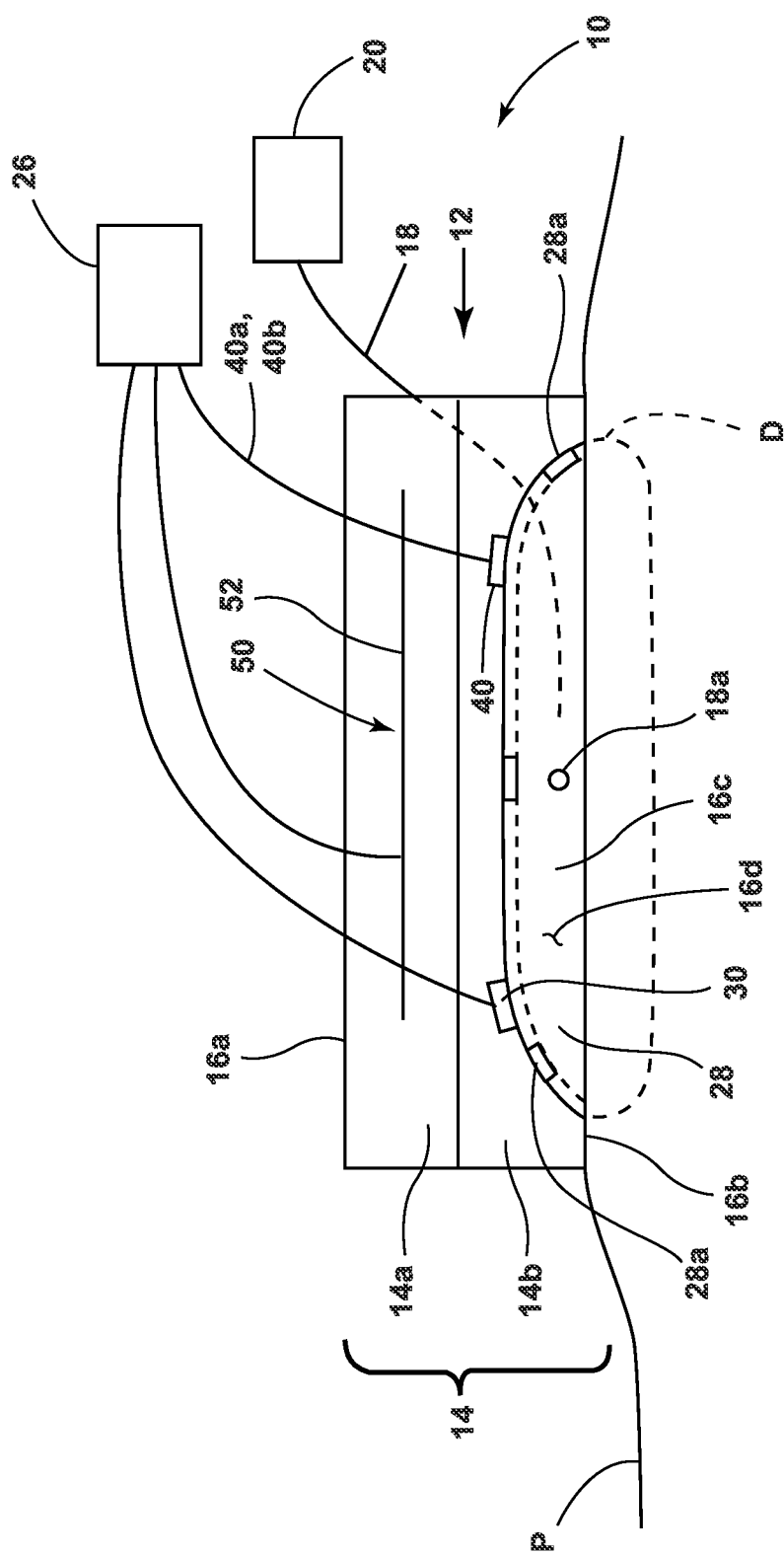
FIG. 1A is cross-section taken along line IA-IA of the apparatus of FIG. 1.

In one embodiment, and referring to FIG. 1A, flexible pad 14 may be formed from two or more layers of material. For example, in one embodiment flexible pad 14 may include two layers 14a, 14b. Layer 14a forms the exterior surface 16a of wearable 12. When recess is used as a closed chamber, layer 14a may comprise an impermeable flexible material, as noted above. When the recess not needed as a closed chamber, layer 14a may comprise a liquid impermeable but gas permeable material, as noted above.

Layer 14b, which forms the tissue facing surface 16b, comprises a flexible material, but also may comprise a soft, cushioning material, such as foam or gel. Layer 14b includes region 16c, optionally formed by a recess 16d. For example, as noted, layer 14b may be formed from a foam or gel, such as a liquid gel (contained in a bladder) or a structural gel, such as a Hydrogel. Optionally, recess 16d may have an insert of highly compressible material, including a highly porous insert, to allow fluid flow to the damaged tissue, as described below. Alternately, a portion of layer 14b may be formed with a highly compressible material, including a highly porous material, such as a reticulated foam, that forms region 16c to provide the pressure redistribution and, optionally, to allow fluid flow to the damaged tissue, as described below. For example, layer 14b may be formed from two materials—one that forms the highly compressible region and the other that forms the remaining portion of the layer 14b, which surrounds the damage tissue and contacts the healthy tissue around the damage tissue.

Optionally, the whole pad or the layer that forms the tissue facing side may be formed and molded to the patient's limb or body, as noted above, including a using 3D printing process, so that it's tissue facing surface follows the surface topography of the limb or body to reduce extrinsic pressure on the damaged tissue and the tissue surrounding the damaged tissue. As more fully described below in reference to FIGS. 3-5, in the case of damaged tissue on a foot, when treating foot ulcer, including a diabetic ulcer, a component or portion of the wearable may be configured as an orthotic.

As noted above, apparatus 10 is configured to apply one or more treatments to the damaged tissue. In one embodiment, wearable 12 is configured to apply a fluid to the wound. For example, the fluid may provide oxygen treatment or therapy to the damage tissue, for example via region 16c. Oxygen may be applied to help the cells of the tissue heal. When cells do not have sufficient oxygen, they can become hypoxic, which can result in slowed granulation of tissue. When oxygen is applied, it is believed to improve granulation and, hence, stimulate healing. Oxygen (O2) may be applied alone or in combination with other elements and/or carriers, and may be generated by chemical reaction, such as hydrogen peroxide in the presence of manganese, which acts a catalyst to speed up the oxygen formation process. Further as noted below, it may be supplied on the form of super oxygenate saline solution or a dressing saturated with a super oxygenate saline solution, as well as hydrogen peroxide noted above, which can be delivered with a constant flow or periodically delivered, e.g. by drip application (liquid form) or bursts of oxygen gas.

In one embodiment, the fluid may include a medicine, such as an antibiotic, such as Neosporin, silver, silver based antibiotics, zinc, and zinc based antibiotics. For example, where the pad has an insert, the insert may be a carrier for the medicine (e.g. the insert may be soaked with the medicine), which can either be replenished or replaced with a new insert and new supply of medicine.

In one embodiment, when region 16c is formed from recess 16d, wearable 12 may include a fluid circuit, such as one or more conduits (e.g. formed by one or more passageways in the wearable or tubing extending through the cover) and an inlet port at the recess so that fluid can be directed into the recess and directed to the damaged tissue. For example, when region 16c is formed a porous insert (made porous either by the material properties of the insert (e.g. reticulated foam) or by the formation of one or more passageways in the insert), the porosity allows the fluid to be directed to the damaged tissue. The oxygen may be applied at a pressure above ambient pressure to increase the pressure in the recess, for example, when the wearable is made from an impermeable material.

Thus, when region 16c is formed by or includes a recess (e.g. recess 16d) aligned over the damaged tissue, the recess may form a closed chamber over the damaged tissue to receive and direct a treatment to the damaged tissue. The treatment, such as oxygen noted above, may be applied using various pressures. For example, as noted, the wearable may be formed from a suitable material that allows the pressure in the recess to be at or above ambient pressure.

For example, oxygen may be applied to the damaged tissue by applying oxygen gas or an oxygen containing liquid, such as super oxygenate saline solution. Optionally, as noted wearable 12 may include a fluid circuit formed by a conduit 18 that is in fluid communication with a supply of oxygen, such as a supply container 20, e.g. a canister, and a valve 22, which is in fluid communication with recess 16d via inlet port 18a. It should be understood that multiple conduits and inlet ports may be provided.

Valve 22, which controls the flow of oxygen through the conduit, may be located in part of the conduit 18 that extends outside the wearable, integrated into container 20, or integrated into the wearable 12 and may comprise a manually operated valve, an electrically operated control valve controlled via a control unit 26, described more fully below, or may be a check valve, depending on the fluid circuit formed by the container and the conduit. For example, as noted below, flow from the container may be controlled by a pump, which when operated by control unit 26 could be used to open the check valve. Further, the flow of fluid may be continuous or periodic, such as drip flow.

Supply container 20 may also be separate from, surface mounted to, or integrated with the wearable 12, and may have a compressed supply of oxygen so that when the valve is opened, oxygen will flow through the conduit and into recess 16d through opening 18a, and onto the damaged tissue. Alternately, the container may be coupled to a pump (coupled to the conduit and to the control unit) to suction the oxygen from the container to control the rate of oxygen flow into the conduit, and into region 16c, such as recess 16d. Valve 22 may, therefore, be optional, or may simply comprise a check valve that opens when the pump is run.

Alternately, the oxygen may be stored in a flexible bladder, with a pump coupled to the conduit (and to the control unit) to suction the oxygen from the bladder and direct the oxygen to recess 16d. The valve may, therefore, be optional in this embodiment as well, or may simply comprise a check valve, as noted, that opens when the pump is run.

Alternately, the oxygen may be provided by a dressing 28 saturated with liquid oxygen. For example, a suitable dressing may include a commercially available dressing OxySpur dressing, which may be placed on the patient's damage tissue, as shown in FIG. 1A, prior to placing wearable 12 over the damaged tissue D. In one embodiment, the dressing 28 may be mounted or integrated into the pad, in region 16c, for example, with dressing 28 attached to pad 14 by releasable fasteners 28a, such as VELCRO strips or adhesive strips, or the like.

Regardless of the form, the oxygen is directed to or near the damaged tissue. When supplied as a liquid or gas, the oxygen may be directed to the damaged tissue at least initially by the tubing, as noted. For example, the tubing may be surfaced mounted or integrated into the apparatus. And when the apparatus has a recess located in the proximity of the damaged tissue, the tubing optionally directs the oxygen into the recess, which in addition to reducing pressure on the damaged tissue then forms a chamber over the damaged tissue between the patient's body and the apparatus (when the apparatus is placed or secured to the patient over the damaged tissue).

In one embodiment, the oxygen may be delivered to the damaged tissue by a separate device, and then the apparatus is placed over the separate device. For example, as noted above, the oxygen may be provided in the form of a dressing, which can either be mounted to the wearable or applied to the damaged tissue, which then is enclosed by the wearable.

In one embodiment, wearable 12 is configured to apply light treatment to the damage tissue and optionally to the entire region or appendage that includes the damaged tissue. The frequency of the light may be selected to optimize treatment. Or light may be applied over the full spectrum of light. For example, when trying to inhibit bacterial growth, UV light may be used. When trying to increase circulation via heat, infrared light may be used.

To apply the light, apparatus 10 may include one or more light sources 30, including light sources of varying frequency, that are in communication with and powered by control unit 26 (see below for more details regarding control unit 26). For example, light may be applied by one or more LEDs. Optionally, the LEDs may be in the form of an array of LEDs, with each LED of the array generating the same wavelength or frequency of light. In one embodiment, the array may include one or more LEDs that generate light at a different frequency. In this manner, the frequency of the array can be adjusted by selective powering of the LEDs by the control system. Further, the array may be extended over the wound only or over the entire skin facing surface of the wearable.

As noted, UV light may be applied to inhibit bacterial growth. To apply the UV light, apparatus 10 includes at one or more UV light sources 30 that are in communication with and powered by control unit 26 (see below for more details regarding control unit 26). For example, light may be applied by one or more UV light sources, such as LEDs. Optionally, the LEDs may be in the form of an array of LEDs, with each LED of the array generating the same wavelength or frequency of light, such as at the UV spectrum of light, namely about $8 \times 10^{14}$ to $3 \times 10^{16}$ hertz (Hz) or about 10 to 380 nm, or one or more generating light at one or more different frequencies (e.g. UVA, UVB, and/or UVC light) wherein the frequency of the LED array can be tunable by adjusting which LEDs are powered to control the wavelength/frequency of the output of the array. For example, in some cases, UVA (e.g. $9.52 \times 10^{14}$-$7.5 \times 10^{14}$ Hz, 315-400 nm) or UVB (e.g. $1.07 \times 10^{15}$-$9.52 \times 10^{14}$, 280-315 nm) light may be applied, and in other cases UVC (e.g. $1.0 \times 10^{15}$-$7.5 \times 10^{14}$ Hz, 300-400 nm) may be more effective. Note that the specific ranges of UVA, UVB, and UVC may vary slightly depending on the technical reference used.

Lights 30 may be integrated into wearable 12, for example, and located in pad 14, for example, at recess 16d to directly apply light onto the damaged tissue, which is located under the recess 16d when wearable is applied to the patient. Alternately, in another embodiment, lights 30 may be surface mounted on wearable 12 and coupled to light pipes, such as optical fibers or tubes, that have light output ends positioned at the upper (as viewed in FIG. 1A) perimeter of the recess so that light is directed into the chamber formed by the recess via the light pipe or pipes. As noted above, the lights may be arranged so that they in effect extend across the entire tissue facing surface of the pad to apply light to the entire area or appendage being treated.

Where region 16c is formed by an insert (or a portion of the tissue facing side of pad 14 formed from softer material), wearable 12 may include a plurality of light pipes that are extended from the respective light source or light sources through the region 16c adjacent the damaged tissue. So as not to interfere with the immersion into region 16c (and the resulting pressure redistribution by the compression of the region 16c), the light output ends of the light pipes may be offset from the contact surface of region 16c and, preferably, located in pockets or small recesses formed in the material, such as the insert, forming region 16c. These pockets or small recesses may be molded in the material forming the region 16d or formed by mechanically removing the material, such as by drilling or cutting.

To protect, a user from overexposure, the control unit 26 may be configured to cease powering the light source(s) when (1) a predetermined a maximum period of time has passed, (2) the applied light reaches a selected maximum dosage, or (3) when a patient's tissue or appendage reaches a selected maximum temperature. For example, the apparatus may include a timer (e.g. a timer circuit or software based timer) and/or sensors in communication with the control unit that detect when the maximum criteria has been reached. Once, the control unit 26 determines based on the timer and/or sensors that the maximum criteria has been reached, control unit 26 will cease powering the light(s).

To protect, a user from accidental unintentional light exposure, for example, UV exposure, the control unit 26 may be configured to only power the light sources when the apparatus is secured to a patient or when a user confirms the apparatus is secured to themselves or to a patient. For example, the apparatus may include one or more sensors (in communication with the control unit) that detect when the apparatus is secured to a patient, either by sensed pressure, or a switch that is activated when the wearable is secured to a patient. Until that sensor reading indicates that the apparatus is secured, control unit 26 may not allow the lights to be powered regardless of input (e.g. pressing of a button, touching an icon associated with the light treatment on a touch screen, for example, etc. described more fully below) by a user.

In one embodiment, wearable 12 is configured to apply electrical stimulation around the damaged tissue, and optionally over a region around the damaged tissue. Referring to FIGS. 1 and 1A, apparatus 10 may include at least two or more electrodes 40 for attaching to a person's limb at or near the damaged skin to apply electrical stimulation to the underlying tissue (via its associated circuitry that is coupled to a voltage source described below), including muscles, nerves, and optionally tendons. Alternately, the electrodes 40 may be applied to a location remote from the damaged skin, for example, over a muscle or nerve that extends into the limb. For example, electrodes 40 may include self-adhesive electrodes, including self-adhesive rubber electrodes, or taped-on electrodes. Optionally, the electrodes may comprises dry fabric electrodes from conductive thread or carbon electrodes for MRI compatibility.

In one embodiment, the electrodes and/or associated circuitry may be screen printed onto the wearable 12. Typically to screen print an electrical component, an insulating layer must be provided. Therefore, depending on the material used to form the wearable, the wearable may include an insulating layer, such as a polymer film, onto which the electrode and/or circuitry may be screen printed.

In another embodiment, the circuitry may be provided on a flexible tape, which is attached to the wearable, and with the electrodes either formed on the tape or on the wearable itself, or separately attached as described above.

Alternately, the electrodes 40 may be applied to a location remote from the damaged skin, for example, over a muscle or nerve that extends into the limb. Reference is made to copending application, U.S. patent application Ser. No. 16/267,635, entitled DEVICES, METHODS, AND SYSTEMS FOR THE TREATMENT OF WOUNDS, filed Feb. 5, 2019, for further examples of suitable locations for the electrodes.

Figure 1B:
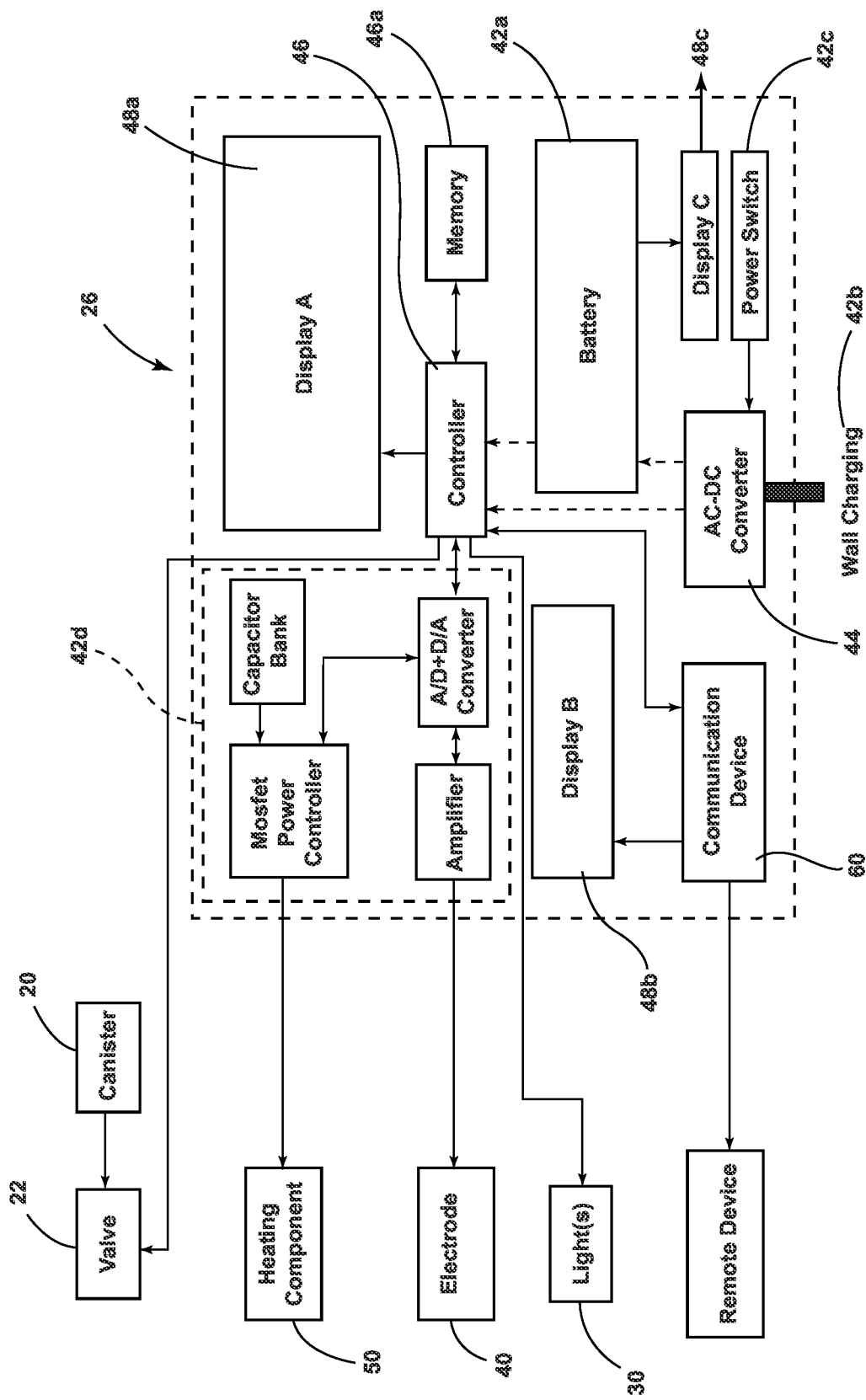
FIG. 1B illustrates a block diagram of a control unit in accordance with an embodiment of the disclosure.

As noted above, apparatus 10 includes a control unit 26. Referring to FIG. 1B, control unit 26 may be powered by a voltage source, such as a battery 42a or other source of current/voltage (such as a standard 120-volt wall outlet 42b) and is in electrical communication with electrodes 40 via electrical leads 40a, 40b (FIGS. 1 and 1A) and configured to supply electrical current to at least one of the electrodes when power switch 42b is activated. Optionally, electrodes 40 may be integrated into or simply be co-located with the wearable 12 (e.g. placed under wearable 12 on skin, but not necessarily attached to the wearable). The voltage source may be provided by on board voltage source, such as a capacitor or a battery, including a rechargeable battery, which may be integrated into the apparatus. For example, control unit 26 may have a control module 42d to control the voltage source to the respective treatment component (s) and/or electrical leads and with a plug configured to couple to an external DC source, such as battery, or an AC source, such as a standard wall AC outlet.

Accordingly, depending on the type of current (AC/DC) and/or voltage provided or delivered to control unit 26, control unit 26 may include a converter (AC to DC or DC to AC) 44 and a transformer to adjust (such as reduce or increase where applicable) the supplied voltage and one or more resistors to adjust (e.g. reduce) the current to suitable levels, described more fully below.

Optionally, control unit 26 includes a controller 46, such as a microprocessor based controller, memory 46a, and a pulse generator (in control module 42c) (at least when apparatus 10 is configured to apply electrical stimulation), which is electrically coupled to the controller and to the source of electricity (either directly or through the controller via electrical leads), which can generate a plurality of electrical impulses for delivering an electrical pulse wave form to the at least one electrode for applying to the person's skin or tissue, to thereby administer the electrical pulse stimulation treatment through electrodes 40. The microcontroller may be a computer on a single integrated circuit and may include one or more CPUs, memory 46a, and programmable input/output peripherals. In some embodiments, an analog-to-digital converter (A/D) is used to read analog sensors that can produce an analog sensor and convert the data to a digital signal that can be recognized by the microcontroller. The digital to analog converter (D/A) may allow the microcontroller to output analog signals or voltage levels.

The microcontroller may be interfaced (in electrical communication) with one or more displays 48a, 48b, and 48c, including an LCD display capable of displaying electrical stimulation waveform, noted below. The output terminal of the amplifier may be connected to the electrodes 40. In this way, the amplifier and associated circuitry can act as a voltage follower with unity gain and provide a high input impedance at the terminal. The output terminal of the MOSFET Power Controller may be connected to the heating component, such as the heating coil or coils. A power MOSFET is a specific type of metal oxide semiconductor field-effect transistor, which are designed to handle significant power levels. In other embodiments, the power semiconductor device may be an insulated-gate bipolar transistor (IGBT). The power MOSFET 502 is a low-voltage (less than 200 V).

In addition, control unit may 26 may comprise one or more user input devices, such as buttons or switches. Optionally, one of the displays (e.g. display 48a) may be formed from a touchscreen to a form a user input device.

In one embodiment, wearable 12 is configured to apply heat to the damage tissue, and optionally over a region greater and beyond just the damaged tissue. Heat may be apply using electrodes 40 or a heating component 50, which may also be controlled by control unit 26. Heating component 50 may be in the form of an electric heating coil 52 (FIG. 1A), including a flexible heating coil, an electronic heater, such as a Peltier device or one or more infrared LEDs, or heated fluid (such as water that flows though channels or tubing), or chemical warmers that when bent or compressed start a chemical exothermic reaction. For example, if using an LED, the infrared LED or LEDs used for heating may be on the same array as the UV LEDs used for applying light treatment or may be a separate array. For example, an array of LEDs may be provided with one set of LEDs providing UV light, and the other set of LEDs providing infrared light so that the LED source (array) is tunable between a UV light output and an infrared light output or output both.

In this manner, the operation of the LEDs can be controlled by control unit 26, which can power all or some of the LEDS at the same time or power them independently to vary the treatment, including the type of UV light and/or the amount of heat that is applied, and any protocol for each treatment.

In one embodiment, heating component 50 may be configured so that it "globally" heats the limb (or portion of the limb or body) that includes the damaged tissue. The term "global" or "globally" refers to raising the temperature of the limb (or portion of the limb) and not just local warming of the limb where the limb surface and the tissue beneath the surface are warmed. To achieve global warming, heat is applied about 40%-100% of the limb or body part (or portion of the limb or body part), and optionally to at least at least 40%, or at least 50%, or at least 60%, or at least 80%, or at least 90%, or about 100%.

In one embodiment, globally warming the limb or body is achieved by wrapping the heating component 14 around the limb (or portion of the limb or body) so that it covers at least 20%, or at least 30%, or at least 40%, or at least 50%, or at least 60%, or at least 70%, or at least 80%, or at least 90%, or about 100% of the limb or body part (or portion of the limb or body part). To that end, wearable 12 is configured to that it is suitable for wrapping around a limb being treated, as more fully described in reference to the embodiment illustrated in FIGS. 3-6.

As noted above, wearable 12 may be in the form of a flexible pad and, further, may be configured as a large patch of material or materials, including fabric, which may be assembled from multiples layers (e.g. 14a, 14b and more), with the heating component 50 sandwiched between two of the layers, or located in a layer, such as layer 14a and shown in FIG. 1A, or in the layer 14b touching the person's skin.

Optionally, in one embodiment, the heating component may comprise a supply of fluid that is warmed and circulated though the apparatus. For example, the fluid may be warmed through a heating device external to the apparatus or a heating device at least partially integrated or mounted to the apparatus. The fluid may be liquid or a gas, such as air. Further, the fluid may be directed through conduits formed in or tubing inserted into the apparatus.

For example, in one embodiment, two or more layers of wearable 14 may be joined together to form a bladder for holding a warming fluid and also to form one or more conduit(s) through which warming fluid may be circulated to the bladder to form the heating component. For example, the conduit may extend to the exterior surface 14a of wearable 12, and to an inlet port formed in wearable 12, for coupling to a supply of warmed fluid.

Additionally, wearable 12 may include a layer of thermally conductive material, for example, to transfer the heat from the heating component 50 to a greater area than the footprint of the heating component and/or a layer of thermally reflective material, either or both of which may increase the efficiency of the heat transfer from the heating component to the limb or body part. To provide an efficient transfer of heat from the heating component 50 to the person's skin, heating component 50 may be located adjacent layer 14ba, which is placed on the person's skin.

Optionally, as noted, to increase the efficiency, one or more of the layers (e.g. layer 14b) may form a thermally conductive layer to transfer the heat from the heating component across the limb—either to provide a more uniform distribution of the heat and/or to facilitate transfer of the heat beyond the immediate "footprint" of the heating component. In one embodiment, one or more of the layers (e.g. layer 14b) may form a thermal insulation layer and may be formed from a heat reflective material, such as heat reflective thin plastic (such as a foil or a thin plastic sheet coated with a metallic reflecting agent, such as metallized polyethylene (MPET)). For further examples of a suitable thermally conductive and/or reflective layer reference is made to copending application, U.S. patent application Ser. No. 16/267,635, entitled DEVICES, METHODS, AND SYSTEMS FOR THE TREATMENT OF WOUNDS, filed Feb. 5, 2019.

In one embodiment, apparatus 10 is configured to apply two or more, and in some cases all, of the treatments noted above.

As noted above, apparatus 10 includes a control unit 26, which is powered by a battery or other source of current/voltage (such as a standard 120-volts wall outlet), and is in electrical communication with the various powered components, such as valve 22 (and/or of the pump), lights 30, electrodes 40, heating component 50, and is configured to supply electrical current to the various components. Accordingly, depending on the type of current (AC/DC) and/or voltage provided or delivered to control unit 26, control unit 26, as noted, may include a converter (AC to DC or DC to AC) 44 and a transformer (not shown) to adjust (such as reduce or increase where applicable) the supplied voltage and one or more resistors to adjust (e.g. reduce) the current to suitable levels, described more fully below.

Further, as noted, control unit 26 may include a controller and memory (42, 42a), which have stored therein software to perform one or more of the various treatments and functions noted herein, including generating a plurality of electrical impulses for delivering an electrical pulse waveform to the at least one electrode for applying to the person's skin or tissue, to thereby administer the electrical pulse stimulation treatment through electrodes 40. Depending on where and how much current is applied, and where the electrodes are placed, the electrical stimulation may induce neuromuscular stimulation (NMES) or transcutaneous stimulation (TENS) or micro tens (MCT) stimulation. Optionally, the pulse generator generates a biphasic pulse waveform, for example, a symmetric biphasic waveform. Again, for further discussion of suitable waveforms, reference is made to the above referenced applications.

Where apparatus 10 is configured for use in a home setting, the pulse generator may generate a biphasic pulse waveform with an amplitude in a range of 1-50 mA (mill amperes), or 10-40 mA, or 15-35 mA, and optionally about 20 mA depending on the desired stimulation. The pulse width may be in a range of 10-1000 µs (microseconds), 50-800 µs, 300-500 µs, again depending on the desired stimulation. For example, for smaller muscles, a suitable amplitude may be around 30 mA and a pulse width may fall in a range of 50-200 µs. For example, for larger muscles, a suitable amplitude may be around 50 mA and a suitable pulse width may fall in a range of 300-500 µs. For nerves, a suitable amplitude may be around 20 mA and a suitable pulse width may fall in a range of 20-100 µs. It should be understood that these are exemplary only, and that the amplitude in milliamps and pulse width varies not only on the type of tissue but the habitus of the tissue being stimulated. The principles fall under the concept of the strength-duration curve. As a result, the amplitude of the current can vary based on the person and/or type of tissue to be stimulated and/or the type of tissue damage that is being treated and/or location of treatment. Further, as noted, the electrical current may be an AC current or DC current, and in some settings a high volt direct current (HVDC).

When configured for use in a medically supervised setting, these values may be adjusted. For example, in medically supervised setting, the pulse generator may generate a biphasic pulse waveform with an amplitude in a range of 0.25 mA to 100 mA, 10 mA to 75 mA, or optionally about 20 mA depending on the desired stimulation. The pulse width may be in a range of 50 to 500 µs, 100 to 300 µs, or optionally about 250 µs, again depending on the desired stimulation. For example, for smaller muscles, a suitable amplitude may be around 20 mA and a pulse width may be around 250 µs. For larger muscles, a suitable amplitude may be around 30 mA and a suitable pulse width may be about 300 µs. For nerves, a suitable amplitude may be around 20 mA and a suitable pulse width may fall in a range of 20-100 µs.

A variety of waveforms can be used in electrical stimulation to target specific areas of the body. In some embodiments, the waveform of the electrical pulse stimulation includes at least one of monophasic, biphasic, asymmetrical biphasic, polyphasic, or pulsed direct current (DC) or high-volt pulsed current, twin spiked waveform or other waveforms or types and combinations of currents may be used. In some embodiments, the current of the electric pulse stimulation includes at least one of sawtooth, trapezoid, triangular, rectangular, spike, or sine shaped waveform.

As would be understood, control unit 26 is therefore constructed of various electrical components that are capable of carrying out the functions described herein. As noted, control unit 26 may include a controller 42, such as a conventional microcontroller or group of conventional microcontrollers. In general, the controller includes any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. When implemented to communicate with a remote device, including a server, a phone, a pad, or other hand held electronic device, as described below in reference to another embodiment illustrated in FIG. 6, the control unit 26 may include a communication device 60, such as a Bluetooth device, a WiFi device, or a USB port, which can provide a communication interface with the remote device, including communication with the Cloud.

Optionally, in addition to electrical stimulation, as noted electrodes 40 may be used to warm the tissue in lieu of or in addition to heating component 50 and, therefore, form the heating component. In order to achieve a warming effect, the pulse generator may generates a pulsed radio-frequency range in the range of 50-500 kHz, with an amplitude in the range of 1 to 100 V or 50 to 100V, and a duty cycle 1% to 100% (pulsed-to-continuous on-time). This could help to heat deep into the limb, especially if you place the electrodes on opposite sides. Further, the pulse generator may be adjustable and configured (e.g. by control unit 26) to switch between an electrical stimulation modality and a warming modality where different waveforms are desired for each desired effect.

Additionally, as will be more fully described below, the wearable or a portion of the wearable may be shaped, such as by molding or by the flexibility/conformability of the material forming wearable 12, to conform to the person's limb or body.

Figure 2:
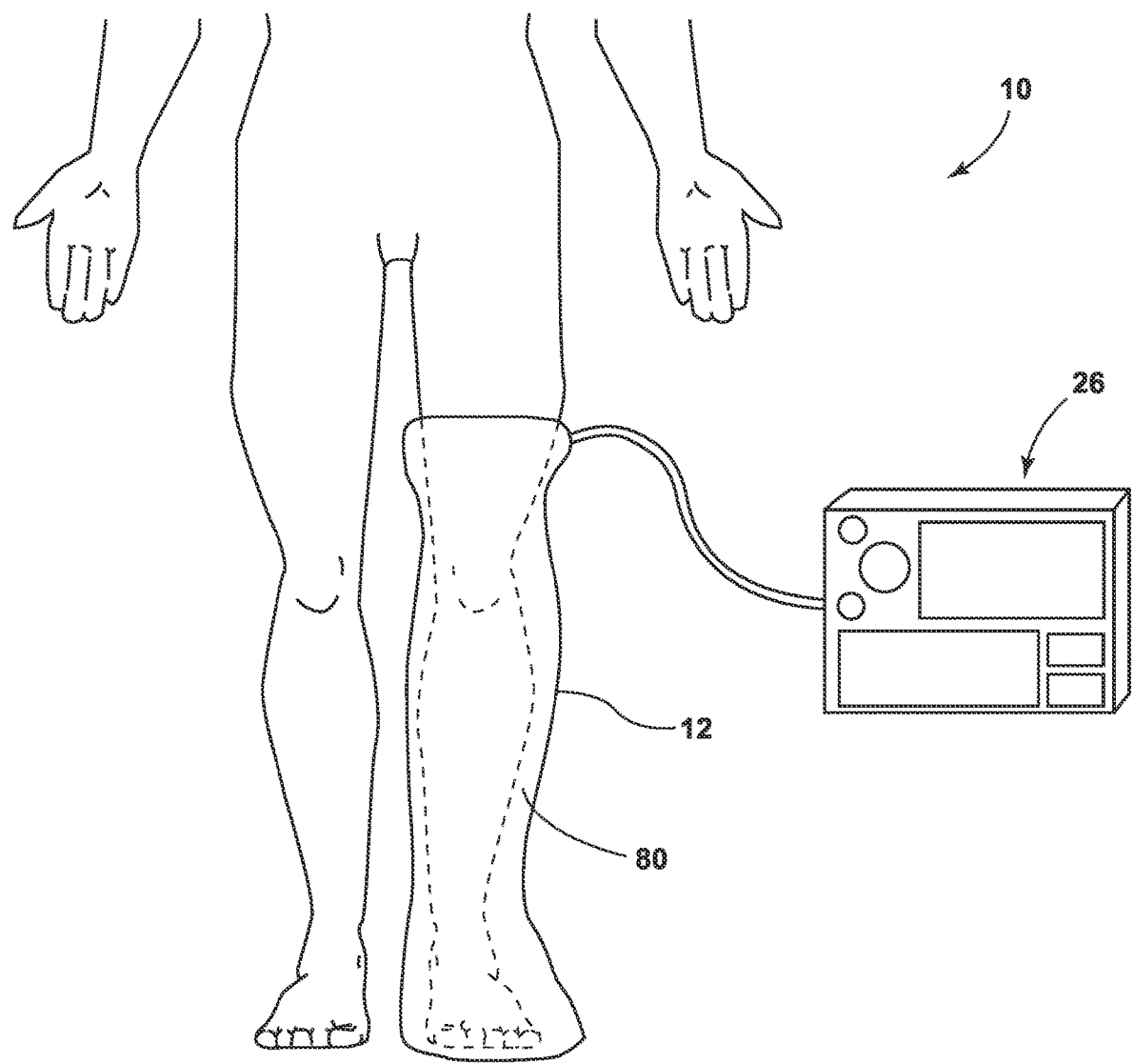
FIG. 2 illustrates another embodiment of the apparatus of FIG. 1 configured into the form of a boot.

For example, as shown in FIG. 2, wearable 12 may be configured into the shape of a boot 80, covering the lower portion of a leg. Boot 80 may start at the knee and extend to, and optionally enclose, the foot, for example, in the case of treating ulcers on the heel of a person. Where the damage tissue is in the foot of the patient, that portion of the wearable that extends under the foot includes region 16c, either in the wearable itself or in an insert, such as described below. Alternately, wearable 12 may be configured as a sleeve to wearable an arm and/or shoulder, or other body part.

Figure 3:
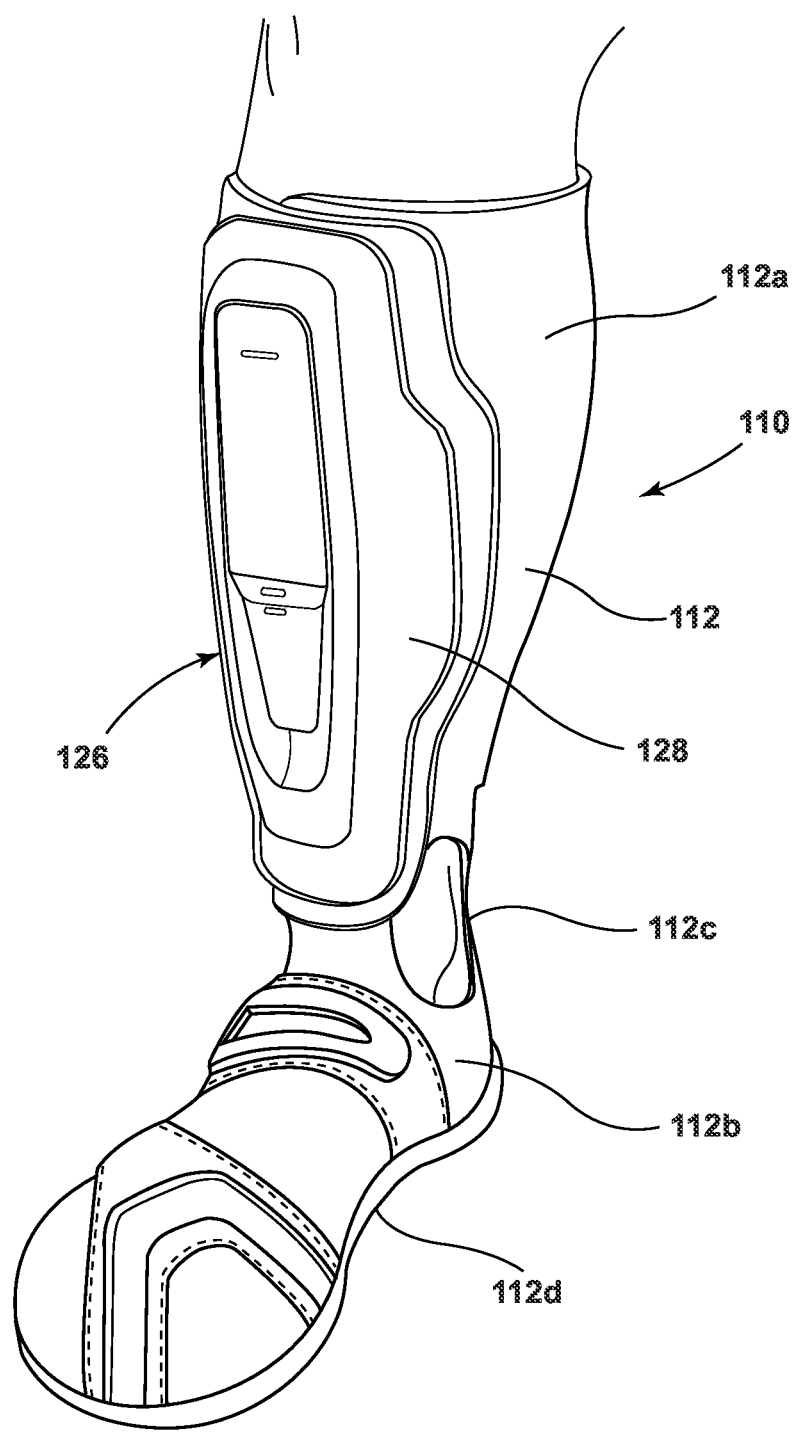
FIG. 3 is a perspective view of another embodiment of an apparatus for treating damaged tissue configured in the form of a boot.

Referring to FIG. 3, the numeral 110 designates another embodiment of apparatus for applying one or more of the treatments to damage tissue. As will be more fully described below, apparatus 110 is also formed from a wearable 112, optionally similar to wearable 12, which incorporates one or more of the above treatment devices. Wearable 112 is configured to apply one or more treatments, in addition to the pressure reduction or redistribution, to the damaged tissue to improve healing of the damaged tissue, for example, by stimulating more blood flow, increasing granulation, reducing hypoxia, and/or by increasing infection control. As described above, the treatments may including applying oxygen, applying electrical stimulation, applying heat, and/or applying light, such as UV light, to or near the damaged tissue.

Further, in one embodiment, apparatus 110 includes an onboard control unit 126, which is mounted to the wearable 112, so that apparatus 110 may be a self-contained unit. Optionally, as will be more fully described below, wearable 112 may have a housing 128 formed thereon with a recess for receiving control unit 126. Further, housing 128 may have one or more electrical connectors, such as USB ports, supported in the recess that is configured to connect to control unit 126 when control unit 126 is inserted into the recess. In this manner, when control unit 126 is inserted into the recess and connected to the electrical connections, to thereby connect the control unit 126 to the various treatment devices, such as the lights (for UV and/or infrared heat treatment), the electrodes for electrical stimulation treatment, and/or a heating component to apply heat treatment. In this manner, control unit 126 may be a plug-in unit that can power the various devices when plugged into the housing recess, but may be removed for repair, replacement, upgrade, or for physically coupling it to another device, such as a computer or smart device, such as smart phone.

In one embodiment, control unit 126 may also include a supply of oxygen, such as a canister, for delivering oxygen for oxygen treatment via ports also formed in housing 128. Alternately, as described above, oxygen may be applied using a dressing, separate or integrated into wearable 112.

Alternately, or in addition, as will be described in reference to FIG. 6, control unit 126 may be configured to wirelessly communicate with another remote device to allow remote control and/or information about apparatus 110 to be shared with a person, such as a healthcare provider who is remote from the patient wearing the device or a third party, such as an insurance company or the product manufacturer for service, upgrades and/or repair.

Figure 3A:
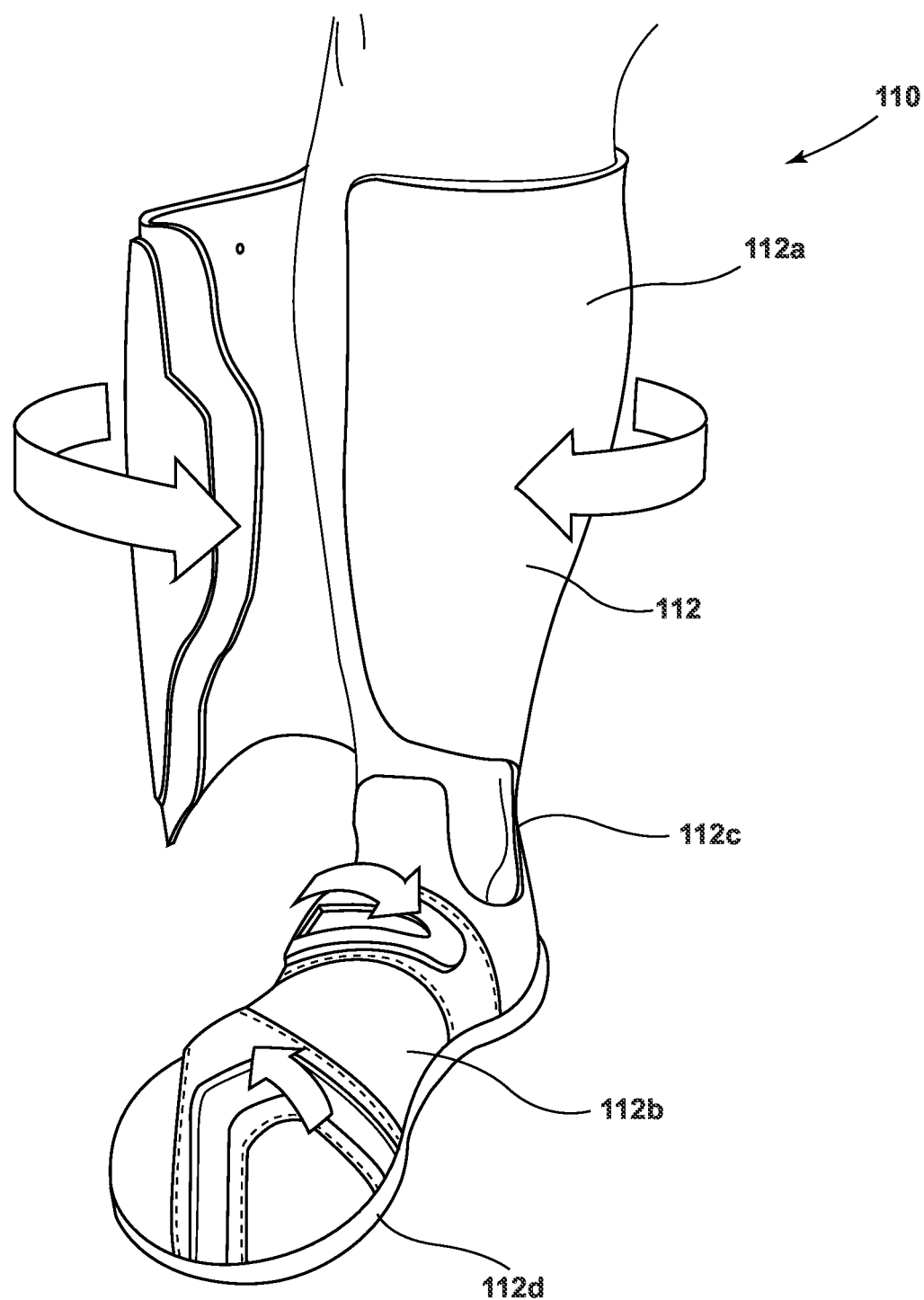
FIG. 3A is a similar view to FIG. 3 illustrating the optional wrap around construction of the apparatus of FIG. 3.

Referring again to FIG. 3 and to FIG. 3A, wearable 112 may be formed from a single unitary pad or from two or more pads that are then joined together to work as a unit. In the illustrated embodiment, wearable 112 is formed from a single pad with an upper portion 112a that is configured to wrap around a limb (for example, a calf), a lower portion 112b that is configured to wrap around the foot and forms or supports a sole 112d, and a connecting portion 112c that joins the upper portion 112a and the lower portion 112b together as a single unit. Connecting portion 112c may have formed there in or support one or more conduits or passageways through which the electrical leads can run so that power can be transmitted from the upper pad portion (where control unit 126 is mounted and supported in housing 128) to the lower pad portion, as described more fully below. Further, connecting portion 112c may support or have other conduits (e.g. tubing) or passageways through which oxygen may be directed to the damage tissue.

Thus, when apparatus 110 is mounted to the patients limb, with the upper portion 112a wrapped around one portion of the limb (e.g. calf), and the lower portion 12b is mounted about the other portion of the patient's limb (e.g. the foot), control unit 126 may be used by the wearer or a caregiver to select and operate the various treatments described above and below.

Figure 4:
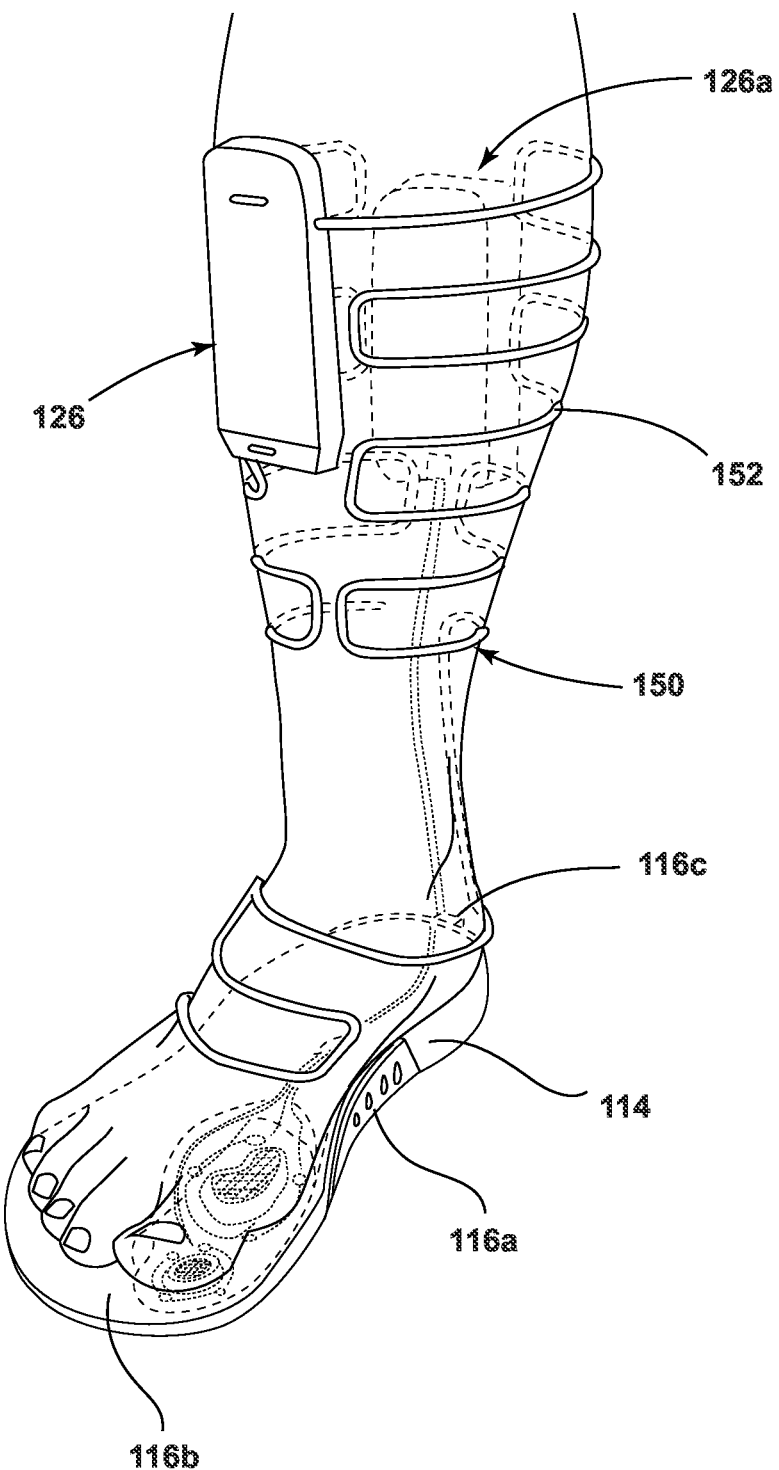
FIG. 4 is a fragmentary view of the apparatus of FIG. 3 with the wearable removed to illustrate one embodiment of a heating component and optional electrical stimulation circuit with electrodes located in an insole of the boot.
Figure 5:
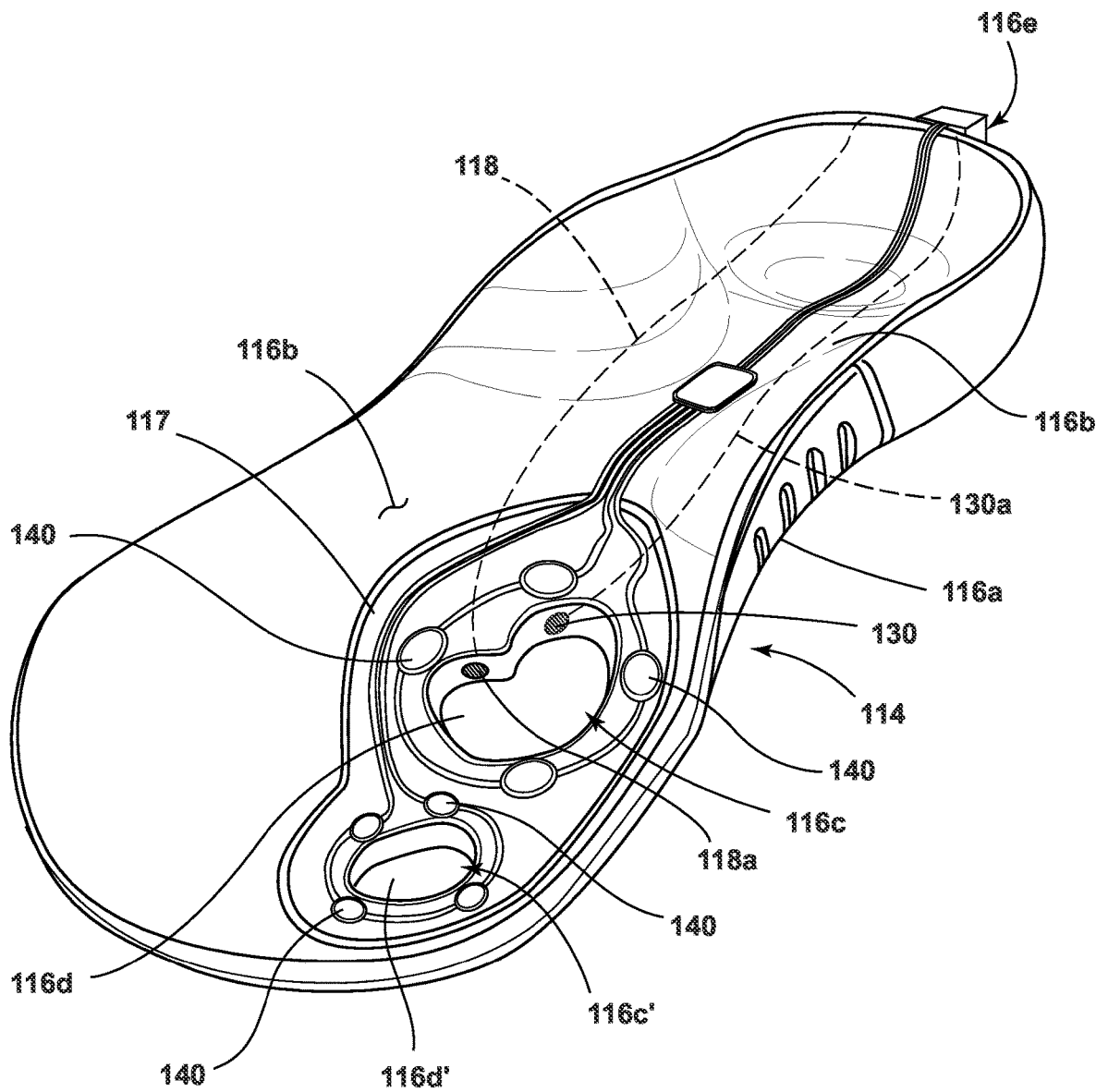
FIG. 5 is an enlarged perspective view of the insole of FIG. 4.

Referring to FIGS. 4 and 5, wearable 112 also may include an insole 114 that is configured to support the foot of the patient. In the illustrated embodiment, apparatus 110 is configured to treat two damaged tissue areas in the foot of the patient and, specifically, in the sole of the patient's foot under and near the large toe. It should be understood that apparatus 110 may also be configured to treat a single area of damaged tissue or more than two areas, and damaged tissue in other areas of the foot.

To reduce pressure on the tissue of the sole, insole 114 is configured to redistribute the pressure from damaged tissue (areas shown in red in FIG. 4) to the surrounding tissue. Referring again to FIG. 5, similar to wearable 12, insole 114 may be formed from a pad of flexible material, such as foam or a gel, that is inserted into wearable 112 and supported on the sole 112d formed by or supported by the lower portion 112b of wearable 112. Insole 114 may be a separate insert that, as will be more fully described below, is customized for the individual patient, or is integral with the sole 112d of the wearable 112.

Referring again to FIG. 5, in one embodiment, insole 114 is a separate insert that includes a bottom side 116a for resting on the inner upper surface of sole 112d and a tissue facing surface 116b on its opposed side. In one embodiment, insole 114 may be molded as an orthotic so that tissue facing side 116b conforms the surface topography of the sole of a patient's foot. In addition, insole 114 includes one or two regions 116c and 116c' that are adapted to at least reduce pressure, if not redistribute pressure, to the surrounding healthy tissue of the patient's foot.

For example, in the illustrated embodiment, each region 116c and 116c' comprises a recess that is sized to extend over and optionally beyond the perimeter of the respective damaged tissue (here two foot ulcers are shown) to reach undamaged tissue. Further, in the illustrated embodiment, regions 116c and 116c' include recesses 116d, 116d' that extend through the insole—though it should be understood that once inserted into the wearable, the recesses will be covered and enclosed on one side by sole 112b of wearable 112. Alternately, the regions 116c and 116c' may be combined (as shown) to form one larger region 117, but in the interest of localizing treatment to each ulcer, the recesses 116d, 116d' are discrete and separate from each other.

As noted above, apparatus 110 is configured to apply a treatment to the damaged tissue. In one embodiment, apparatus 110 is configured to apply light treatment to the damage tissue. To apply the light treatment, apparatus 110 includes one or more light sources 130, for example, that are located in one or both recess 116d and 116d'. For example, light sources 130 may be located in the insole 114 and in the portion of the insole (e.g. side wall) that surrounds the recesses 116d, 116d' or may be located in the sole 112d so that the light is directed at the damaged tissue directly.

Light sources 130 are in communication with and powered by control unit 126 via electrical leads 130a, which may extend through insole 114. For example, leads 130a may extend through insole 114 and couple to an electrical connector 116e, such as a USB connector, provided on insole 114, which when inserted into wearable 112 couples to a corresponding electrical connector, such as a USB connector, near the bottom of lower portion 112b of wearable 112, which in turn couples to electrical leads extending though wearable 112 (e.g. through connection portion 112c) and to control unit 126, either directly or through one of the electrical connectors formed in housing 128, as noted above, or to a separate control unit 126a (FIG. 4). For details and optional components of control units 126 and 126a, reference is made to control unit 26.

Light sources 130 may generate UV light to apply UV treatment to the damaged tissue, as noted above in reference to wearable 12. For example, when light sources 130 are located in the insole, to facilitate the UV light impinging on the damaged tissue, the upper surface of sole 112d may have a reflective surface formed thereon under the recesses 116d, 116d', such as a metalized surface or a thin sheet of metal, such as aluminum. Alternately, or in addition, each light source may include a lens that redirects the light towards the damaged tissue.

For example, light sources 130 may comprise one or more UV light sources, such as LEDs. Optionally, as noted above, the LEDs may be in the form of an array of LEDs, with each LED of the array generating the same wavelength or frequency of light, such as at the UV spectrum of light or one or more generating light at one or more different frequencies wherein the frequency of the LED array can be tunable by control unit 126 by adjusting which LEDs are powered to control the frequency of the output of the array.

Alternately, in another embodiment, lights 130 may be surface mounted on wearable 112 and coupled to light pipes, such as optical fibers or tubes, that have output ends positioned at the perimeter of the recess 116d, 116d' so that light is directed into the chamber formed by the recess 116d, 116d' and the sole of the patient. As noted above, to protect a user from accidental UV light exposure, the control unit 126 may be configured to only power the UV light sources when the apparatus is secured to a patient or when a user confirms the apparatus is secured to themselves or to a patient.

In one embodiment, lights 130 are configure to apply heat to the damaged tissue and thereby may form a heating component. For example, lights 130 may comprise infrared light sources, such as infrared LEDS. For further details of an alternate embodiment of a heating component, reference is made to FIG. 4 and its associated description.

Referring to again to FIG. 5, apparatus 110 may be configure to apply electrical stimulation. Optionally, wearable 112 includes at least two or more electrodes 140 for attaching to a person's limb at or near the damaged skin to apply electrical stimulation to the underlying tissue, including muscles, nerves, and optionally tendons. In the illustrated embodiment, electrodes 140 are located in insole 114, and are optionally located around each recess 116d, 116d' to apply electrical stimulation to the healthy tissue surrounding the damaged tissue.

Alternately, other electrodes may be separately used at locations remote from the damaged skin, for example, over a muscle or nerve that extends into the limb. In another example, the electrodes may be incorporated into upper portion 112a of wearable 112. For further details about suitable electrodes and location of the electrodes reference is made above to wearable 12 and to the reference application.

In one embodiment, apparatus 110 is configured to apply oxygen to the damage tissue, for example in recess 116d, 116d'. Similar to wearable 12, oxygen (O2) may be applied alone or in combination with other elements and/or carriers, and may be generated by chemical reaction, such as hydrogen peroxide as noted above. Further as noted, it may be supplied on the form of super oxygenate saline solution, including using a dressing saturated with a super oxygenate saline solution, as well as hydrogen peroxide, which can be delivered with a constant flow or periodically delivered, e.g. by drip application (liquid form) or bursts of oxygen gas.

In the illustrated embodiment, oxygen is applied to the damaged tissue by applying oxygen gas or an oxygen containing fluid, such as super oxygenate saline solution, and directing the oxygen to recesses 116d, 116d'. Optionally, wearable 112 includes a fluid circuit formed by a conduit 118 that is in fluid communication with a supply of oxygen and recesses 116d, 116d' via a port 118a (FIG. 5), which may be located in one or both recesses and/or also in the larger recessed region 117 described above. For example, control unit 126 may include a supply container 120 (such as a canister) or the supply container may be mounted separately to wearable 112. To control the flow of oxygen, the fluid circuit may include a valve and/or a pump, as described above in reference to apparatus 10, which are controlled by control unit 126. For other examples of how oxygen can be supplied, including the use of dressings, reference is made to apparatus 10.

In one embodiment, the oxygen may be delivered to the damaged tissue by a separate device and then the apparatus is placed over the separate device. For example, as noted above, the oxygen may be provided in the form of a dressing, which can either be mounted to the wearable or applied to the damaged tissue, which then is enclosed by the wearable.

In one embodiment, as noted wearable 112 may be configured to apply heat to the damage tissue, and optionally over a region beyond just the damaged tissue. Heat may be apply using the lights 130 noted above or electrodes 140, or a heating component 150, which may also be controlled by control unit 126.

In the illustrated embodiment, heating component 150 may be in the form of an electric heating coil 152 (FIG. 4), including a flexible heating coil, which is mounted in at least upper portion 112a of pad, and optionally also in lower portion 112b of wearable 112. In the illustrated embodiment, coil 152 is looped through upper portion 112a and then extended to lower portion 112b to heat the calf as well as the top of the patient's foot. Coil 152 is electrically coupled (optionally hardwired) to control unit 126 or via the electrical connections described above located in housing 128.

In this manner, the heating component 150 may be configured so that it "globally" heats the limb (or portion of the limb or body) that includes the damaged tissue. The term "global" or "globally" refers to raising the temperature of the limb (or portion of the limb) and not just local warming of the limb where the limb surface and the tissue beneath the surface are warmed.

As noted above, wearable 112 may be in the form of a flexible pad and, further, with an upper portion 112a and a lower portion 112b, as well as connection portion 112c. As best understood from FIG. 3A, upper portion 112a may be sized so that when it is wrapped around the calf of the patient, it will have overlapping portions sufficiently large to provide a mounting surface for fasteners, such as VELCRO strips or the like, to provide easy securement of the upper portion 112a about the calf and also to provide adjustment to accommodate patient's with different size legs and calves. In other word—one side of the upper portion is larger than the other side so that it can form the overlapping portion, and in effect act as a strap when it is secured as noted above. Additionally, the outermost overlapping portion of upper portion 112a may provide a mounting surface for housing 128 (and control unit 126). The optional additional control unit 126a may be mounted to the section of the upper portion that extends behind the calf (as view in FIG. 3A, and best seen in FIG. 4).

Similarly, lower portion 112b may be configured so that is too provides an overlapping arrangement, again with a sufficient overlap to provide a mounting surface for fasteners, such as VELCRO strips or the like, to provide easy securement of the lower portion 112a about the foot and also to provide adjustment to accommodate patient's with different size feet. Further, lower portion 112b may have two enlarged lobes with one closer to the ankle and the other located over the toes of the wearer, which in effect form straps to secure the lower portion to the foot.

Referring again to FIG. 3A, when putting on apparatus 110, wearable 112 is first fully unfolded so that a person can place their foot on the insole 114 (see FIG. 4). Once the foot is placed on the insole, one side of the lower portion 112b is placed over the foot, followed by the other side. The lobe of the lower portion closest to the ankle first secured in place, followed by the second lobe. Once the lower portion is secured, the upper portion 112a can then be wrapped around the person's calf, with the larger portion of the upper portion placed over the shorter portion.

In any of the above apparatuses, the apparatus may include one or more sensors in communication (electrical or wireless) with control unit 26, 126, and or 126a. For example, in some embodiments, the sensors may be separate, discrete sensors or may be screen printed onto the wearable. In various embodiments, the plurality of sensors include at least one of Doppler probes, Hall Effect probes, skin temperature probes, and a differential high voltage probe. Doppler probes are capable of measuring blood flow. In some embodiments, a wide-band Hall Effect sensor is used to monitor current. Skin temperature probes are capable of monitoring the temperature of the skin at treated sites. Differential high voltage probes can record voltage in real-time.

Similar to the electrodes, the sensors may be separately mounted from the wearable, co-located with the wearable, or integrated with the wearable 12, 112. For example, similar to electrodes 40, 140 the sensors may be located at the tissue facing surface of the wearable, for example, by surface mounting or flush mounting them to or in tissue facing surface. When separately mounted or co-located with the wearable, the sensors may be mounted to the skin of the person using an adhesive strip or an adhesive, including an adhesive with a very low pull force required for removable, such as a conductive adhesive gel, including HYDROGEL, which is tacky enough to hold a small device, such as a sensor, in place, especially when then covered by the wearable, but is easily removed to avoid damage to the person's skin.

The sensors may be used to sense and, optionally, measure one or more physiological conditions of a person undergoing treatment and forward sensor signals to the microprocessor of the control unit, containing measurement data, for processing. In some embodiments, the data from the sensor signals may be sent to a remote location, for example, for monitoring the wound. For more details or additional examples of how the sensors may be used, reference is made to the above reference related application.

Figure 6:
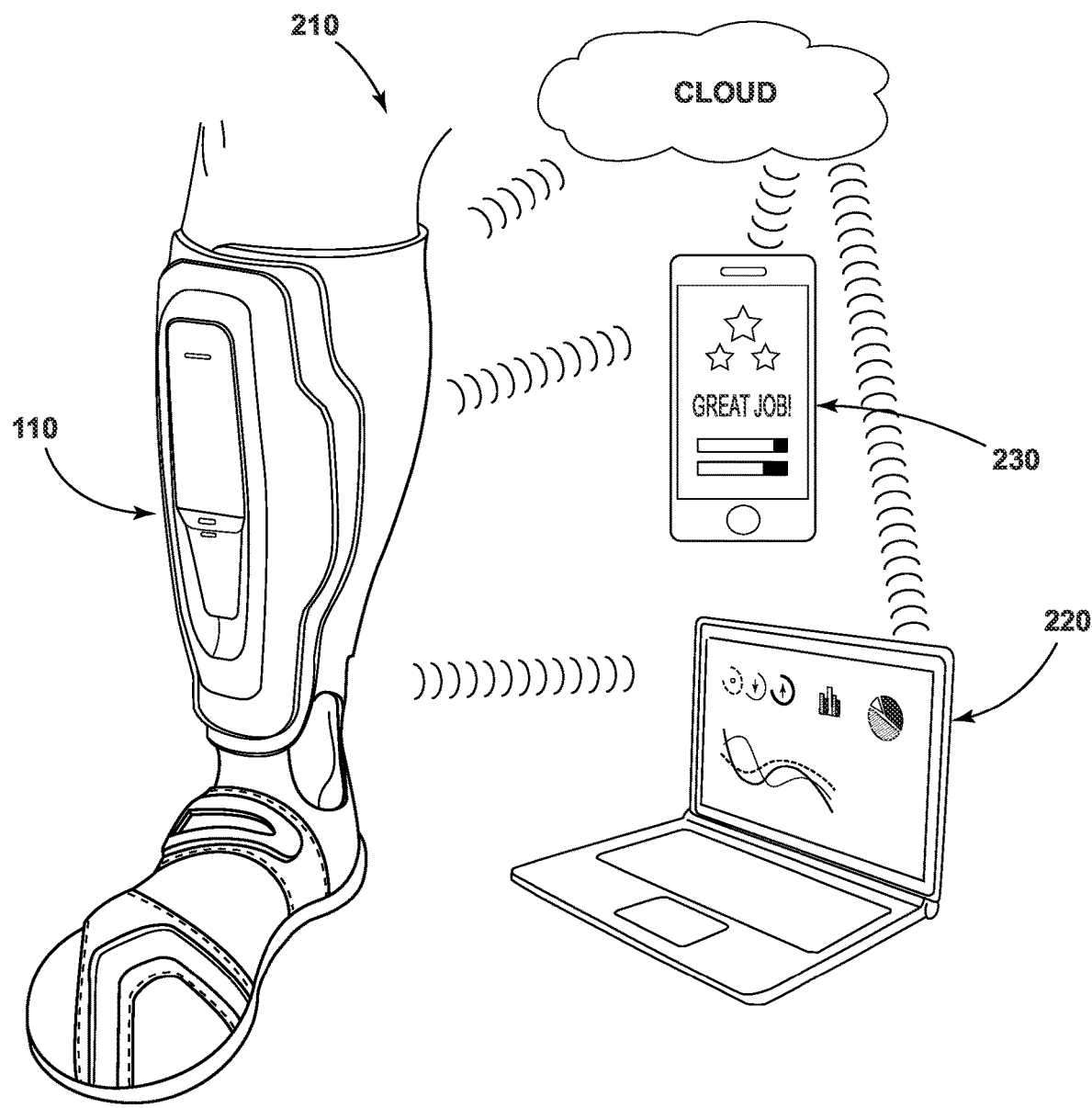
FIG. 6 is a schematic drawing of a therapeutic system including the therapeutic apparatus of FIG. 3 and optional remote control devices, such as a computer and/or a smart device, such as smart phone.

Referring to FIG. 6, the numeral 210 illustrates an embodiment of a therapeutic treatment system. System 210 includes apparatus 110 and one or more remote devices 220, 230. As noted above, control unit 126 may include a communication device 60 (described in reference to control unit 26). Communication device 60 may comprise a wireless communication device, such as RF transceiver, for exchanging signals, such as control signals and/or data, with remote device 220 and/or remote device 230. For example, remote device 220 may comprise a computer, such as a lap top computer, and remote device 230 may comprise a smart device, such as a smart phone. Further, any of the communication device 60, remote device 220, and/or remote device 230 may communicate with the Cloud to upload and store data.

Such remote devices may also include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Depending on the proximity of the remote devices, the communication device may comprise a Bluetooth device for exchanging control signals and/or data over short distances from fixed and mobile devices. The Bluetooth module may be configured to exchange data with local monitors provide in apparatus 110 (or 10), for example, a blood flow monitor, a heart rate monitor, a thermometer, all available for use as input to control unit 26, 126 or for simple forwarding to the remoted device, including via the Cloud.

Therefore, in certain embodiments, it should be understood that any of the apparatuses described herein may be part of a system in which the use of the apparatus may be controlled and/or information about the use of the apparatus may be monitored, tracked, and/or recorded on a computer or a server or the Cloud.

While the present disclosure has been described in reference to certain embodiments, numerous modifications, alterations and changes to the described embodiments are possible without departing from the scope and spirit of the present invention. Accordingly, it is intended that the present invention not be limited to the described embodiments. Nor is the invention limited by the listed claims.

We claim:

1. A therapeutic apparatus for treating damaged tissue on a limb or body portion of a subject, said therapeutic apparatus comprising:
    a wearable adapted to cover and be secured to the limb or body portion of a subject over damaged tissue, said wearable configured to contact the limb or body portion around the damaged tissue but being configured to off-load pressure from the damaged tissue but in the presence of atmospheric pressure; and
    said wearable adapted to apply electrical current to induce electrical stimulation and to globally warm the limb or body portion at the same time as applying the electrical current to raise the temperature of the limb or body portion and not just provide local warming of the damaged tissue wherein at least 40% of the limb or body portion is warmed.

2. The therapeutic apparatus according to claim 1, wherein said wearable includes a recessed region that extends over the damaged tissue and makes no contact with the damage tissue to thereby off-load pressure from the damage tissue.

3. The therapeutic apparatus according to claim 1, wherein said wearable includes at least two electrodes that are located so that they contact the skin of the patient around or adjacent the damage tissue when the patient is wearing the apparatus, and wherein said at least two electrodes are configured to apply said electrical current and induce said electrical stimulation to the skin of the patient surrounding or adjacent the damaged tissue.

4. The therapeutic apparatus according to claim 2, further comprising an electrical pulse generator in electrical communication with an electrical supply and electrically coupled with said electrodes, said electrical pulse generator being configured to generate electrical pulse stimulation with said at least two of said electrodes and configured to apply the electrical pulse stimulation with a biphasic wave form in a range of 1 mA to 50 mA with a pulse width in a range of 50 to 500 microseconds.

5. The therapeutic apparatus according to claim 1, wherein said wearable covers an extent of a limb and further includes an insulation layer to distribute heat over the extent of the limb.

6. The therapeutic apparatus according to claim 5, wherein the insulation layer comprises a foil.

7. The therapeutic apparatus according to claim 6, wherein said foil forms a passive warming system to warm the limb.

8. The therapeutic apparatus according to claim 2, wherein said apparatus is adapted to supply oxygen to the damaged tissue in the recessed region.

9. The therapeutic apparatus according to claim 8, wherein said wearable includes a conduit adapted to couple to an oxygen source surfaced mounted or integrated into the wearable to supply oxygen to the damaged tissue.

10. The therapeutic apparatus according to claim 9, wherein said recess forms a chamber over the damaged tissue when the therapeutic apparatus is applied the patient over the damaged tissue.

11. The therapeutic apparatus according to claim 6, in combination with a separate device for supplying oxygen to the damaged tissue, and said wearable being configured to extend over the separate device and to be secured to the subject over the separate device.

12. The therapeutic apparatus according to claim 1, further comprising a UV lamp to directly or indirectly apply UV light to the damaged tissue.

13. The therapeutic apparatus according to claim 1, further comprising one or more sensors, at least one sensor being configured to (1) measure at least one indicator of wound healing, (2) track of the use of the device and/or (3) track the condition of the subject.

14. The therapeutic apparatus according to claim 13, further comprising a transmitter for sending information, about or relative to the apparatus or the patient to a remote computer, a handheld device, a nurse call station, and/or a server.

15. The therapeutic apparatus according to claim 1, wherein said wearable is configured to cover at least the foot of the subject, said wearable being configured to conform to the patient's foot and including a recess in the region of the damaged tissue to off-load pressure on the damaged tissue.

16. A therapeutic apparatus for treating damaged tissue on a limb or body portion of a subject, said therapeutic apparatus comprising:
    a wearable to cover and be secured to the limb or body portion of the subject over damaged tissue, and said wearable being configured to off-load pressure from the damaged tissue;
    a pair of electrodes to apply electrical stimulation to the damaged tissue; and said wearable being adapted to apply one or more treatments selected from the group consisting of (1) heat wherein the heat applies global warming to the limb or body portion of the subject, (2) oxygen wherein the oxygen is directed to the damaged tissue, and (2) light wherein the light is directed to the damaged tissue.

17. The therapeutic apparatus according to claim 16, wherein when said wearable has a recess in the region of the damaged tissue to off-load pressure and thereby reduce pressure on the damaged tissue, and further comprising a UV lamp to directly or indirectly apply UV light to the damaged tissue.

18. The therapeutic apparatus according to claim 17, further comprising one or more sensors, at least one sensor being configured to measure at least one indicator of wound healing.

19. The therapeutic apparatus according to claim 17, further comprising one or more sensors, at least one sensor being configured to track of the use of the device and/or condition of the subject.

20. The therapeutic apparatus according to claim 19, further comprising a transmitter for sending information about or relative to the apparatus or the subject to a remote computer, a handheld device, a nurse call station, and/or a server.

21. The therapeutic apparatus according to claim 20, wherein said wearable is adapted to supply oxygen to the damaged tissue.

22. The therapeutic apparatus according to claim 16, wherein said wearable is configured to cover at least the foot of the subject, said wearable being configured to conform to the subject's foot and including a recess in the region of the damaged tissue to off-load pressure and thereby reduce pressure on the damaged tissue.

23. The therapeutic apparatus according to claim 13, wherein at least one sensor is configured to (1) track of the use of the device and/or (2) track the condition of the subject.

24. The therapeutic apparatus according to claim 16, wherein said wearable is adapted to apply globally warming to the limb or body portion and not just provide local warming of the damaged tissue wherein at least 40% of the limb or body portion is warmed.

* * * * *